US 6,436,040 B1

United States Patent
Collamore et al.

(10) Patent No.: US 6,436,040 B1
(45) Date of Patent: Aug. 20, 2002

(54) INTUITIVE USER INTERFACE AND CONTROL CIRCUITRY INCLUDING LINEAR DISTANCE MEASUREMENT AND USER LOCALIZATION IN A PORTABLE ULTRASOUND DIAGNOSTIC DEVICE

(75) Inventors: Brian Collamore, Rutland; Rachel M. Kinicki, Acton; Donald W. Lewallen, Andover; Grace M Saccardo, Bolton; Janice M Blackwell-Jones, N. Andover; Peter Koester Rhoads, Stow, all of MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/710,609

(22) Filed: Nov. 9, 2000

(51) Int. Cl.[7] ................................................. A61B 8/00
(52) U.S. Cl. ....................................... 600/437; 600/459
(58) Field of Search ................................ 600/443, 437, 600/447, 459, 460

(56) References Cited

U.S. PATENT DOCUMENTS

| | | |
|---|---|---|
| 5,590,658 A | 1/1997 | Chiang et al. |
| 5,603,323 A | 2/1997 | Pflugrath et al. |
| 5,636,631 A | 6/1997 | Waitz et al. |
| 5,690,114 A | 11/1997 | Chiang et al. |
| 5,715,823 A | 2/1998 | Wood et al. |
| 5,722,412 A | 3/1998 | Pflugrath et al. |
| 5,817,024 A | 10/1998 | Ogle et al. |
| 5,839,442 A | 11/1998 | Chiang et al. |
| 5,851,186 A | 12/1998 | Wood et al. |
| 5,879,303 A | 3/1999 | Averkiou et al. |
| 5,891,035 A | 4/1999 | Wood et al. |
| 5,893,363 A | 4/1999 | Little et al. |
| 5,897,498 A | 4/1999 | Canfield et al. |
| 5,938,607 A | 8/1999 | Jago et al. |
| 5,957,846 A * | 9/1999 | Chiang et al. ............... 600/447 |

(List continued on next page.)

Primary Examiner—Francis J. Jaworski
Assistant Examiner—Maulin Patel
(74) Attorney, Agent, or Firm—John Vodopia (57) ABSTRACT

An ultrasound diagnostic device includes a console portion and a display portion. The console portion includes a control panel, which includes a plurality of input keys. A user may input commands on the control panel by actuating one or more keys on the control panel. The console portion comprises control circuitry, which controls the operations of the ultrasound diagnostic device. The control circuitry receives input signals from the control panel. The input signals correspond to commands entered by the user on the control panel. The control circuitry processes the electrical signals and performs operations on an ultrasound image being displayed on a display monitor. The ultrasound images being displayed on the display may be modified by the control circuitry in response to one or more keys of the control panel being actuated by the user. A transducer assembly connected to the console portion is used by the user to acquire ultrasound image information from a subject. Each of the keys on the console portion represent a particular function to be performed by the control circuitry on image information acquired by the transducer assembly. This "one button per function" feature of the invention utilizes icons, which inform the user of the function of each key. This feature of the invention renders the control panel suitable for use all over the world since the icons are capable of being understood by people of different nationalities. The overall size and weight of the ultrasound diagnostic device is reduced because the number of keys needed to operate the ultrasound diagnostic device is minimized. In another aspect of the invention, the ultrasound diagnostic device includes logic configured to allow the device to be localized by the user based on a number of different parameters, including, but not limited to, language, date appearance convention and decimal point convention.

22 Claims, 8 Drawing Sheets

U.S. PATENT DOCUMENTS

| | | |
|---|---|---|
| 5,964,709 A | 10/1999 | Chiang et al. |
| 5,997,479 A | 12/1999 | Savord et al. |
| 6,007,490 A | 12/1999 | Pawluskiewicz |
| 6,013,032 A | 1/2000 | Savord |
| 6,102,863 A | 8/2000 | Pflugrath et al. |
| 6,106,468 A | 8/2000 | Dowdell |
| 6,106,472 A * | 8/2000 | Chiang et al. ............... 600/447 |
| 6,113,547 A | 9/2000 | Catallo et al. |
| 6,117,084 A | 9/2000 | Green et al. |
| 6,117,085 A | 9/2000 | Picatti et al. |
| 6,132,379 A * | 10/2000 | Patacsil et al. ............. 600/459 |
| 6,135,961 A | 10/2000 | Pflugrath et al. |
| 6,139,499 A * | 10/2000 | Wilk .......................... 600/443 |

\* cited by examiner

INTUITIVE USER INTERFACE AND CONTROL CIRCUITRY INCLUDING LINEAR DISTANCE MEASUREMENT AND USER LOCALIZATION IN A PORTABLE ULTRASOUND DIAGNOSTIC DEVICE

TECHNICAL FIELD

The present invention relates to an ultrasound diagnostic device and, more particularly, to an ultrasound diagnostic device having a unique user interface and control circuitry including linear distance measurement and user localization ability in a portable ultrasound diagnostic device.

BACKGROUND OF THE INVENTION

Portable ultrasound systems are known in the ultrasound equipment industry. U.S. Pat. No. 5,722,412, issued on Mar. 3, 1998 to Advanced Technologies Laboratories, Inc., of Bothell, Wash., discloses such a system. Although the known portable ultrasound systems have been designed to facilitate ease of use and portability, none of the known systems provide a total solution in terms of ergonomics, imaging acquisition and processing, and display image quality. For example, a system might be easy to carry because it is relatively small, but cumbersome to operate because the user must manipulate the ultrasound transducer, which may be a rather bulky piece of equipment, with one hand, while holding the ultrasound diagnostic device in the other hand. Even if the user does not hold the ultrasound diagnostic device, but rather, places it on a stable surface, the user may have difficulty viewing the image due to limitations relating to the adjustability of the display.

To provide another example, even if the ultrasound diagnostic device has good adjustability with respect to the display, the enclosure may be designed such that it must be placed on a relatively stable, flat surface when not being held by the user. In some environments, such as at the scene of an automobile accident, a stable, flat surface may not be available. This may result in the user having to hold the ultrasound diagnostic device in one hand while using the other hand to manipulate the transducer of the ultrasound diagnostic device. This prevents the user from being able to use a hand to steady themselves while obtaining diagnostic measurements, which may be important in certain environments.

Other shortcomings of today's ultrasound diagnostic devices is that the amount of information required to be supplied by the user can be excessive. Typically, ultrasound diagnostic device user interfaces are modeled on a "menu driven" approach. In such user interfaces, each function key or input device may have multiple functions. These functions are typically accessed through the use of menus that are presented to the user on the display of the device. While typically providing much detail and many options with respect to the ultrasound diagnostic device, these menus are also typically complicated and not easily understood and navigable by someone having only a modest level of understanding and experience with ultrasound diagnostic device controls.

Another shortcoming of ultrasound diagnostic devices is that, while these devices are sold in many countries, the above-described menu-driven interface does not easily lend itself to localization in different countries. For example, if an ultrasound diagnostic device is sold in multiple countries, a different version of the user interface is required for each country. In the past, ultrasound products have been localized by creating different product versions for different local languages. Unfortunately, this necessitates translation into multiple languages and requires that multiple software versions, multiple keypad language indicators and multiple display conventions, depending on the country in which the device is sold and operated, be created. This in turn requires that multiple configurations of the same ultrasound diagnostic device be manufactured, tested, stocked, and maintained, thus increasing cost and complicating production.

These are only examples of some of the shortcomings of known portable ultrasound diagnostic systems. These examples demonstrate that none of the known systems provide an overall solution in terms of ergonomics, ease of use by those having limited experience with ultrasound diagnostic equipment, imaging acquisition and processing capability, image display quality, and user localization. Accordingly, a need exists for a portable ultrasound diagnostic device which meets all of these goals.

SUMMARY OF THE INVENTION

The invention provides an ultrasound diagnostic device for acquiring and processing ultrasound images. The device comprises a console portion and a display portion. The console portion comprises a control panel, which comprises a plurality of input keys. A user may input commands on the control panel by actuating one or more keys on the control panel. The console portion comprises control circuitry, which controls the operations of the ultrasound imaging device. The control circuitry receives input signals from the control panel. The input signals correspond to commands entered by the user on the control panel. The control circuitry processes the signals and performs operations on an ultrasound image being displayed on a display. The ultrasound images being displayed on the display may be modified by the control circuitry in response to one or more keys of the control panel being actuated by the user. A transducer assembly connected to the console portion is used by the user to acquire ultrasound image information from a subject.

Each of the keys on the console portion represent a particular function to be performed by the control circuitry on image information acquired by the transducer assembly. This "one button per function" feature of the invention utilizes icons, which inform the user of the function of each key. This feature of the invention renders the control panel suitable for use all over the world by those having limited experience with ultrasound diagnostic equipment since the icons are capable of being understood by those having limited ultrasound diagnostic experience and by people of different nationalities. The size and weight of the system are reduced by simplifying the system by offering the user the minimal set of controls necessary to obtain a diagnostic quality ultrasound image.

In accordance with another aspect of the invention, the ultrasound diagnostic device includes logic configured to allow the device to be localized by the user based on a number of different parameters, including, but not limited to, language, date appearance convention and decimal point convention.

Other systems, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The present invention can be better understood with reference to the following drawings. The components within the drawings are not necessarily to scale relative to each other, emphasis instead being placed upon clearly illustrating the principles of the present invention.

DETAILED DESCRIPTION OF THE INVENTION

Although the present invention will be described below with particular reference to a particular portable ultrasound diagnostic device, the user interface, localization feature, and other related features of the invention are applicable to many other ultrasound diagnostic device designs.

Elements of the invention can be implemented in hardware, software, firmware, or a combination thereof. In the preferred embodiment(s), elements of the user interface, localization and related features of the invention are implemented using a combination of hardware and software or firmware that is stored in a memory and that is executed by a suitable instruction execution system. If implemented in hardware, as in an alternative embodiment, the invention can be implemented with any or a combination of the following technologies, which are all well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The software portion of the invention, which comprises an ordered listing of executable instructions for implementing logical functions, can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM or Flash memory) (electronic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

Figure 1:
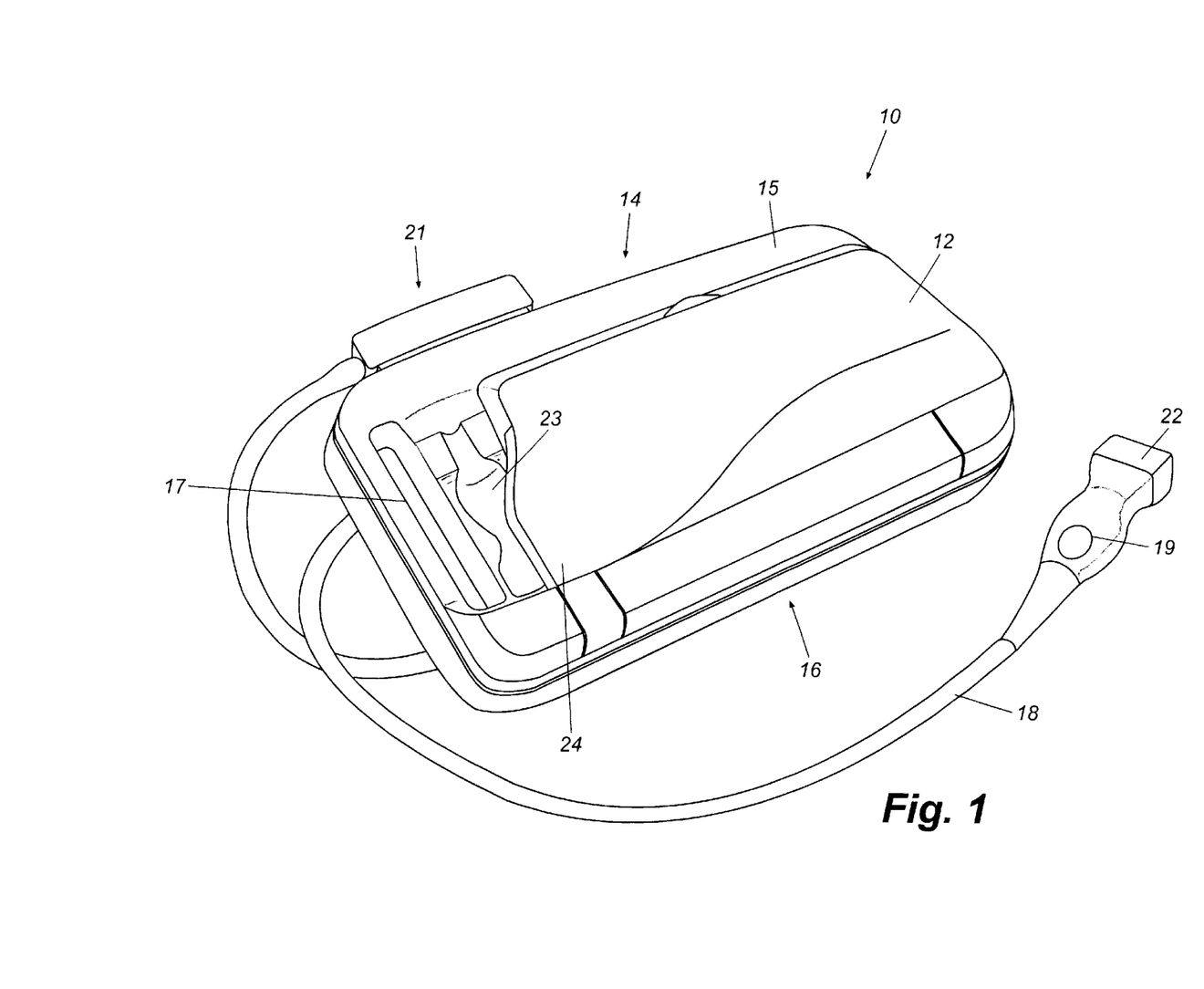
FIG. 1 is a pictorial representation of an ultrasound diagnostic device constructed in accordance with the invention.

FIG. 1 is a pictorial representation of the ultrasound diagnostic device 10 of the present invention. The ultrasound diagnostic device 10 of the present invention preferably is 13½ inches long, 9.5 inches wide and 3.5 inches thick, although those skilled in the art will understand that the present invention is not limited to these exact dimensions. The weight of the device 10 preferably is less than 7.7 pounds, including the control circuitry, the battery pack, the carrying strap and the transducer assembly, which are all discussed below in detail. The manner in which this lightweight design has been achieved in accordance with the invention is attributable to the overall design and construction of the device 10 and to the judicious selection of electrical and data storage components implemented in the device 10, as discussed below in more detail.

The device 10 is similar in design to a laptop computer, except that it is smaller than many typical laptop computers. The device 10 comprises a console portion 15 and a display portion 12. To open the device 10, the user opens the display portion 12 by unlatching and lifting up on the display portion 12 at a location near the front end 14 of the device 10. The display portion 12 is in a hinging relationship with the console portion 15 so that when the user lifts up on display portion 12, the display portion 12 is rotated upwards (i.e., away from the console portion 15). The hinging relationship is provided by a hinging mechanism (not shown) which couples the display portion 12 to the console portion 15 at one or more locations adjacent a rear surface 16 of the ultrasound diagnostic device 10. The hinging mechanism may be similar to hinging mechanisms typically used with laptop computers currently available on the market.

A transducer assembly is removably connected by a connector 21 to the ultrasound diagnostic device 10 and comprises a transducer cable 18, a transducer handle 19, and a transducer 22. The connector 21 comprises a latch (not shown) which engages a mating mechanism (not shown) comprised in a receptacle (not shown) formed in the console portion 15. Preferably, the transducer handle 19 is small enough to fit comfortably in the palm of the hand of the user so that a user can easily manipulate it.

The connector 21 enables different types of transducer assemblies to be implemented with the ultrasound diagnostic device 10. Depending on the bodily feature being imaged, different transducer assemblies can be utilized with the ultrasound diagnostic device 10. The user can easily unplug one type of transducer assembly and easily plug another transducer assembly into the receptacle. Of course, each transducer assembly must be adapted to mate with the receptacle. This provides the ultrasound diagnostic device 10 with great flexibility with respect to its applications, as will be understood by those skilled in the art. For example, a cardiologist doing rounds at a hospital may use the ultrasound diagnostic device 10. Rather than using a stethoscope to check patients' heart beats, the cardiologist may connect the appropriate transducer assembly to the device 10 and use the device 10 in the same manner in which a conventional stethoscope is used. In contrast, a gynecologist may use the ultrasound diagnostic device to perform fetal monitoring. In this case, a transducer assembly, which is suitable for this purpose, will be plugged into the receptacle.

The transducer handle 19 and transducer 22 are designed to fit within a recess 23 in the console portion 15 and is covered by an extended portion 24 of the display portion 12 when the display portion 12 is closed over the console portion 15. When the system closes, the power is turned off automatically. The console portion 15 also includes an integrated handle 17, which includes a recess configured to provide storage of the transducer cable 18. In use, the user may, for example, set the ultrasound diagnostic device 10 on a patient's bed, rotate the display portion 12 to an appropriate viewing position, turn on the device 10, and manipulate the transducer handle 19 to image the patient's heart. Although not shown, the ultrasound diagnostic device 10 may also include a carry strap.

When the ultrasound diagnostic device 10 is intended to be used with transducer assemblies that are implemented for different imaging purposes, the ultrasound diagnostic device 10 comprises software and/or hardware that is capable of acquiring and processing the various types of imaging information. The ultrasound diagnostic device 10 may be switched between imaging applications, which correspond to different transducer assemblies. In this case, the ultrasound diagnostic device 10 may or may not comprise different software driver modules for each of the different transducer assemblies.

The ultrasound diagnostic device 10 comprises a central processing unit (not shown), e.g., a microprocessor, which controls the operations of the ultrasound diagnostic device 10. When the user switches from one application (as used herein, the term "application" refers to different uses, e.g., cardiology, ob/gyn, etc., while the term "mode(s)" refers to black and white (B/W), color, doppler, etc.) to another, the central processing unit (CPU) simply executes the appropriate software module to enable the central processor to acquire and process the image data obtained by the transducer assembly, as will be understood by those skilled in the art. The software modules may be stored in a system memory device (not shown) which is in communication with the CPU. Alternatively, whenever a particular transducer assembly is to be used, the user can load an appropriate software module into the system memory device via some type of data input device (not shown), such as, for example, a magnetic disk, CD ROM drive, or other removable memory and storage media.

Figure 2:
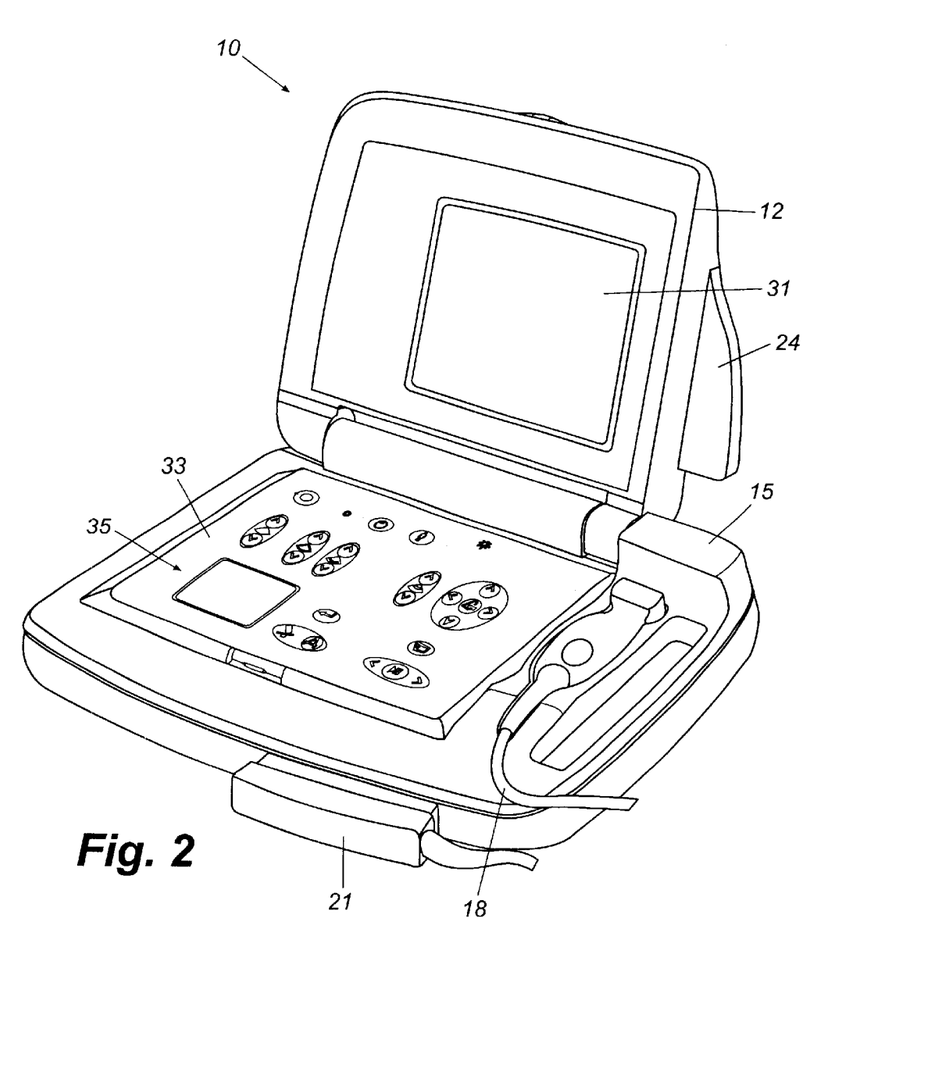
FIG. 2 illustrates the ultrasound diagnostic device of FIG. 1 with the display portion placed in a viewing position.

FIG. 2 illustrates the ultrasound diagnostic device 10 of FIG. 1 with the display portion 12 placed in a viewing position. Preferably, the display screen 31 included in the display portion 12 is a full-color liquid crystal display (LCD) screen, or other type of full color display. Preferably, the display screen 31 is large enough to provide a high quality image and is small enough to maximize the portability of the ultrasound diagnostic device 10. As will be understood by those skilled in the art, the display screen 31 is not limited to any particular dimensions. The console portion 15 comprises a small control panel 33 having a number of keys 35. Each of the keys 35 includes an icon that is descriptive of the key's functionality. By using icons on the keys, a single control panel 33 can be used in different countries around the world because the icons have been selected so that the meanings of the icons generally are well known to those who perform ultrasound diagnostic imaging tasks, as will be understood by those skilled in the art. Furthermore, by using keys having universally understood icons, the localization aspect of the invention, which will be discussed in greater detail below, becomes easier and more practical to implement. The icons will be discussed in greater detail below.

Figure 3:
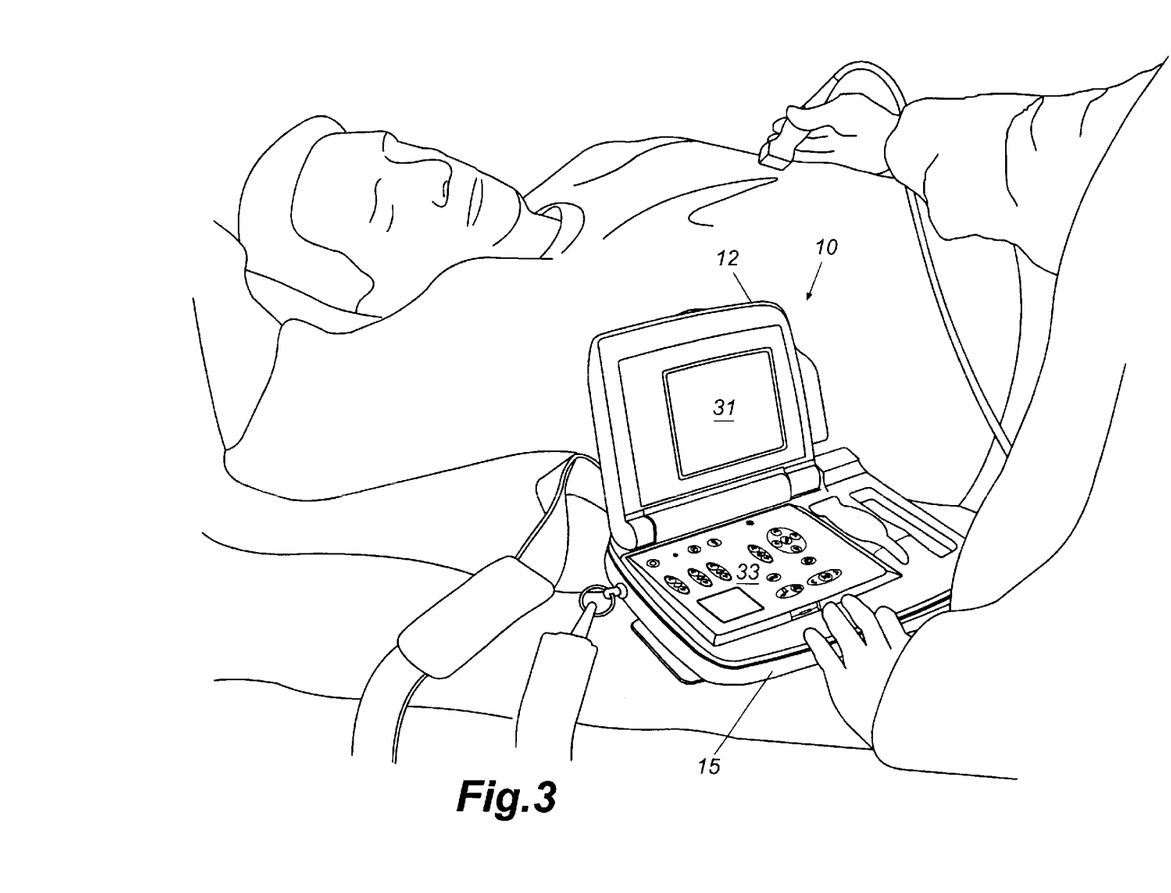
FIG. 3 illustrates the ultrasound diagnostic device of FIG. 1 when placed on a surface, such as the bed of the patient, when the user is performing diagnostic measurements.

FIG. 3 illustrates the ultrasound diagnostic device 10 when placed on a surface, such as the bed of the patient, when the user is performing diagnostic measurements. Preferably, the ultrasound diagnostic device 10 comprises a non-skid pad (not shown) which is affixed to one or more locations on the bottom surface of the device 10. The non-skid pad inhibits movement of the device 10 when it is placed on slanted and/or slick surfaces. This is advantageous in emergency situations where the environment or settings may not provide ideal surfaces. For example, the user may need to place the device 10 on the hood of a car in the rain. In such a situation, the non-skid pad inhibits movement of the device 10.

Preferably, the display portion 12 and the console portion 15 are comprised of cast metal and molded plastic to provide the ultrasound diagnostic device 10 with a rugged encasement. The ultrasound diagnostic device 10 is designed to withstand external impact resulting from, for example, dropping the device 10 or collisions between the device 10 and external objects. Furthermore, the ultrasound diagnostic device 10 folds, as described above, such that when it is not in use the display screen 31 and the control panel 33 are protected from external forces. The transducer connector 21 is also designed of the same or similar types of materials so that it can also withstand shocks from external forces. These features of the ultrasound diagnostic device 10 ensure reliability and reduce the possibility of damaging the device 10 in the field, which is especially important in emergency situations. Also, by increasing the reliability of the instrument, maintenance service requirements are reduced, thereby potentially increasing cost savings.

Figure 4:
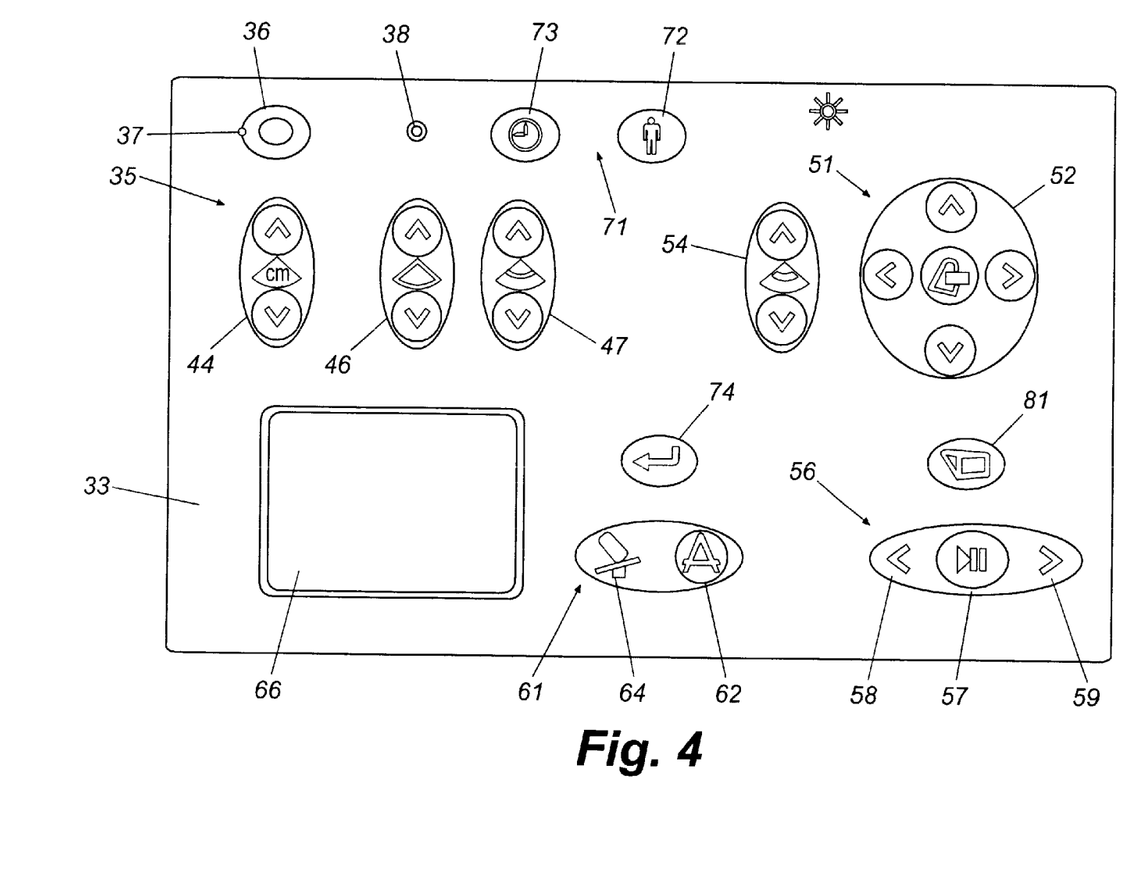
FIG. 4 is a plan view of the control panel of the ultrasound diagnostic device of FIG. 1.

FIG. 4 is a plan view of the control panel 33 of the ultrasound diagnostic device 10 of FIG. 1. As shown in FIG. 4, icons have been placed on the keys 35 of the control panel to facilitate ease of use of the device 10. In accordance with an embodiment of the invention, all system imaging controls are "one button-one function," i.e., each key corresponds to a command which tells the central processor to perform a particular function. The keys 35 preferably are logically and ergonomically grouped in such a manner that they can be easily identified and so that their meanings are self-evident. Furthermore, by minimizing the number of control keys, the user interface is intuitive. Each control on the control panel 33 has only one function during ultrasonic imaging. The intuitive user interface is particularly useful when those having limited experience with such diagnostic devices are using the ultrasound diagnostic device. By limiting the functionality of the ultrasound diagnostic device 10 to a subset of all possible ultrasound imaging functions, those having limited skill are able to use the ultrasound diagnostic device 10.

Typically, users of the ultrasound diagnostic equipment receive extensive training and become highly skilled in the use of the equipment. These individuals are referred to as "sonographers." Unfortunately, these highly trained sonographers are not always available to operate the equipment. Furthermore, portable ultrasound diagnostic equipment can be useful for many diagnostic functions. An intuitive user interface as described herein allows those having limited experience with the ultrasound diagnostic equipment to effectively use the equipment and obtain high quality ultrasound images.

In addition, there are two cases where a combination of two keys will activate other functionality. Due to the choice of the activating buttons, neither of these two functions will be activated during ultrasonic imaging. Instead, the two functions are intended for set-up and support purposes. The two functions are: (1) access to the localization screens, which are only activated when the user receives the ultrasound imaging system 10 and desires to localize the system (will be described below) and (2) activation of the support screen, which provides system information when the user determines that service of the ultrasound diagnostic device 10 is required.

Localization of the ultrasound diagnostic device 10 refers to the ability to configure the device depending on the country in which it is to be used and includes adjusting the patient identification (id) function, date format and decimal point format, as will be described in detail below. For example, by having internationally recognizable icons on the keys 35, a minimal amount of translation is required to allow the device 10 to be used in different countries. System software and the control panel are the same for each language. Repeating the control panel icon on the imaging screen to denote the active value makes the value easily identifiable.

The user can illuminate the keys, or controls, on demand by activating a switch (not shown) on the control panel 33. Alternatively, the ultrasound diagnostic device 10 may comprise a light sensor which senses the level of illumination and which causes the controls to be illuminated when the level of illumination drops below a predetermined level.

An exemplar embodiment of the control panel 33 will now be discussed with reference to FIG. 4. It should be noted that the control panel 33 is not limited to the buttons and icons shown in FIG. 4. The buttons and icons shown in FIG. 4 will be discussed for the purposes of demonstrating the intuitive "one key per function" feature of the invention. Also, it is not necessary that buttons be used on the control panel 33. Any kind of actuation device(s) can be used on the control panel 33 to allow a user to input data and/or commands on the control panel 33. Preferably, all of the buttons are membrane keys, as will be understood by those skilled in the art. The use of membrane type keys prevents spills of ultrasonic diagnostic gel or other fluids from damaging the keys. Similarly, the use of a touch-pad 66 to allow user interaction with the ultrasound diagnostic device 10 minimizes the potential for damage caused by contamination by preventing fluid seepage into the mechanism. Furthermore, the use of the touch-pad 66 enables the ultrasound diagnostic device 10 to have a low profile as there are no device actuators, such as joysticks, pointer button, trackball, or the like, protruding from the surface of the flat touch-pad 66.

The controls on the ultrasound diagnostic system 10 are divided into several logical groups. Each group is arranged together on the control panel 33. Where applicable, the same icon used on the control panel 33 is repeated on the image screen display 31 with the appropriate control value.

In the exemplar embodiment shown in FIG. 4, the control panel 33 includes an on/off button 36. Two illumination devices (i.e., lights or light emitting diodes) 37 and 38 positioned near the on/off button 36 inform the user as to when the device 10 is on or off and when the device 10 is in an internal diagnostic testing mode. The light 37 goes on when the power is turned on and goes off when the power is turned off The other light 38 goes on when the internal tests complete satisfactorily.

The 2-dimensional (2D) imaging controls are used to adjust the 2D image. The pie-shaped icon 44 which has the characters "cm" printed inside and up-arrow and down-arrow signs, represents the image sector, which is commonly referred to as a B-mode image sector, seen by the user on the display monitor. The button 44 is used to adjust the depth of the image being displayed by changing the distance from the face of the transducer to the deepest point in the displayed image. For example, if the depth of the image being displayed is 16 centimeters and the user desires to view an image at a depth of from 0 to 8 centimeters (cm) in the body, the user depresses the button 41 at a location on the down-arrow sign. The display monitor will display information corresponding to the depth of the image being displayed.

The two buttons 46 and 47 are gain variance control buttons. The user uses these buttons to control what is commonly referred to as time gain compensation (TGC). The control circuitry comprises a time gain amplifier (not shown) which varies gain with respect to time. As acoustical energy is propagated into the body by the transducer, the body absorbs some of the energy, while some of the energy is reflected back out of the body and received by the transducer. The strength of this echo will vary depending on the distance between the object that caused the echo and the transducer. Therefore, in many cases it is desirable or necessary to amplify the echoes. The button 46 is used to control the overall gain of the image being displayed. To decrease the gain, the user depresses the button 46 at a location on the down-arrow sign. To increase the gain, the user depresses the button 46 at a location on the up-arrow sign.

The button 47 is used to increase and decrease the gain of echoes that correspond to targets in the top section of the displayed image. This section of the displayed image corresponds to targets that are relatively close to the transducer. The user obtains the desired amplification of the image sector by depressing the button 47 on the up or down-arrow signs.

The color control group 51 is used to activate "color flow imaging," adjust color flow gain, and position the color wedge within the 2D sector. The color control button 52 is utilized to position a superimposed Color Flow Doppler image over the B-Mode image being displayed on the display monitor. In ultrasound imaging, colors are utilized to represent velocity. The well-known Doppler effect is utilized to determine the velocity of the target being imaged and to encode the velocity data with colors. For example, if blood is flowing towards the transducer, the blood is typically represented in shades of yellow and red on the display monitor, depending on the velocity of the blood. If blood is flowing away from the transducer, it is typically displayed in shades of blue on the display monitor. For example, if the user were viewing a vessel in which all the blood is flowing away from the transducer, the vessel would be colored blue. If the user were viewing a vessel in which all of the blood is moving towards the transducer, the vessel will be colored yellow or red, depending upon the velocity.

The color control button 52 allows an image sub-sector that is colored to be superimposed over the B-mode image sector being displayed. The B-mode image may be, for example, a sector image that is 90 degrees in width. The button 52 allows the user to shift the superimposed color sector to any one of several fixed locations over the B-mode image sector by using the arrow keys. The color control button 52 toggles the device 10 between black and white and color flow imaging modes. The four arrow keys allow repositioning of the color flow window by moving the fixed size color flow window to different locations within the black and white image. The color gain button 54 adjusts the color flow receive gain within the color wedge.

The review control group 56, which includes freeze button 57, which resembles a "playstop" function, back (<) button 58 and forward (>) button 59 allow the user to review and store previously acquired images. The freeze button 57 is actuated by the user in order to freeze an image being displayed on the display monitor and toggles the device 10 between real-time and frozen imaging modes. For example, if an image is being displayed on the display monitor at a rate of 30 frames per second, activating the freeze button 57 will freeze the last image that was being displayed when the freeze button 57 was activated. Entering the freeze mode activates the image review mode, where back button 58 can be used to scroll back through saved images and the forward button 59 can be used to scroll forward. The control circuitry will cause this image to continue to be displayed until the freeze button 57 on the console is reactivated. In the exemplar embodiment, when the freeze button 57 is activated a second time (i.e., toggled), the device 10 will resume displaying the images in real time as they are acquired. The icon associated with the freeze button 57 is a universal symbol, which facilitates ease of use of the ultrasound diagnostic device by the user. The button 81 having the folder icon can be actuated to save the displayed image to either internal memory or to a removable memory element.

The measurement control group 61 is used to make linear measurements on a displayed image. The functions of the buttons 62 and 64 and touch-pad 66 will be described with respect to obtaining a linear measurement of the distance between two locations on an imaged item. The linear measurement system uses the caliper button 62 in conjunction with the touch-pad 66 to obtain multiple linear measurements.

When the button 62, having the icon of a pair of calipers thereon, is depressed, a first mark in the form of a colored "X" appears on the display screen 31. For example purposes only, the first color can be red. In addition to the first red X, another graphic, which represents a depth marker anchor (at the image apex) and which provides the user with a dynamic display of the depth in cm from the transducer surface to the first red X, will also appear on the display screen 31. The user manipulates the touch-pad 66 to move the first red X to a desired first location. When the first red X is at the desired location, the user again presses the caliper button 62 at which time the first red X is frozen at the desired location and a second mark in the form of a second red X appears on the screen. The depth marker and its associated value is erased. Along with the second red X is another graphic display, which dynamically displays the distance between the first and second red X's in cm. The user again manipulates the touch-pad 66 to position the second red X over the endpoint of the distance to be measured, at which time the user again presses the caliper button 62, thus freezing the second red X. At this time, the display of the distance between the two red X's is also frozen on the screen. The touch-pad 66 allows continuous x/y position control of the on-screen markers during measurement. If the position of the second red X approaches the first red X, the two marks are reduced in size to prevent the red marks from obstructing the image.

When the position of the second red X is frozen, another mark, in the form of a plus (+) sign having a second color is displayed to initiate a second linear distance measurement. For example purposes only, the second color can be yellow. Along with the first yellow plus sign, another depth marker anchor and dynamic distance display corresponding to the second set of marks (yellow plus signs) is displayed. The user positions the first yellow plus sign where desired and again actuates the caliper button 62. The first yellow plus sign is frozen and a second yellow plus sign appears on the display. The second linear measurement takes place in a similar method to that described above. It should be noted that the colors of red and yellow are used for illustrative purposes only.

The two caliper marks can be deleted using the erase button 64. When the erase button 64 is first actuated, the yellow "+" marks and measurement value disappear from the display screen 31. When the erase button 64 is again actuated the red X marks and measurement values disappear. It is also possible to "undelete" the caliper measurements. The erased caliper marks, signs, and values are stored in memory and can be recalled by actuating the caliper button 62. As mentioned above, when the caliper button 62 is actuated, a first red X appears. If the caliper button 62 is again actuated before the touch-pad control is used to move the red X, the red X's will be displayed in their previous positions and the associated measurement values will be displayed. Similarly, if the caliper button 62 is again actuated before the touch-pad is manipulated, the yellow "+" marks and measurement value will be recalled and displayed.

The identification group 71 allows the user to enter the patient identification (id) using button 72 and to set the date and time using button 73. Because these controls are not used during imaging, they are located away from the imaging controls. The touch-pad 66 and the select button 74, together with either the patient id button 72 or the date/time entry button 73 allow the user to enter the appropriate patient id information, date and time.

Additional buttons (not shown) located on the control panel 33 or as icons on the display screen 31 can be incorporated to provide discipline specific functionality. For example, for obstetrics, a button having the icon of a baby's head thereon, or located on the display screen 31 and actuated using the touch-pad 66, may activate a software module that displays several obstetric calculation icons on the display screen 31. Using the touch-pad 66, the user may choose the type of obstetric calculation (e.g., gestational age based on head circumference) that he or she wants to compute and the system generates the calipers and ellipses necessary for that calculation. The user positions these appropriately over the correct image screen location in order to complete the calculation. Of course, the icon of the baby's head may be replaced by a different icon if the ultrasound diagnostic device is intended to be used for some other type of ultrasound imaging task, such as imaging of a heart. In this case, an icon of a heart could be placed on the button. The icon of the baby's head has been used in this example because it is a well-recognized icon in the ultrasound imaging industry.

Figure 5A:
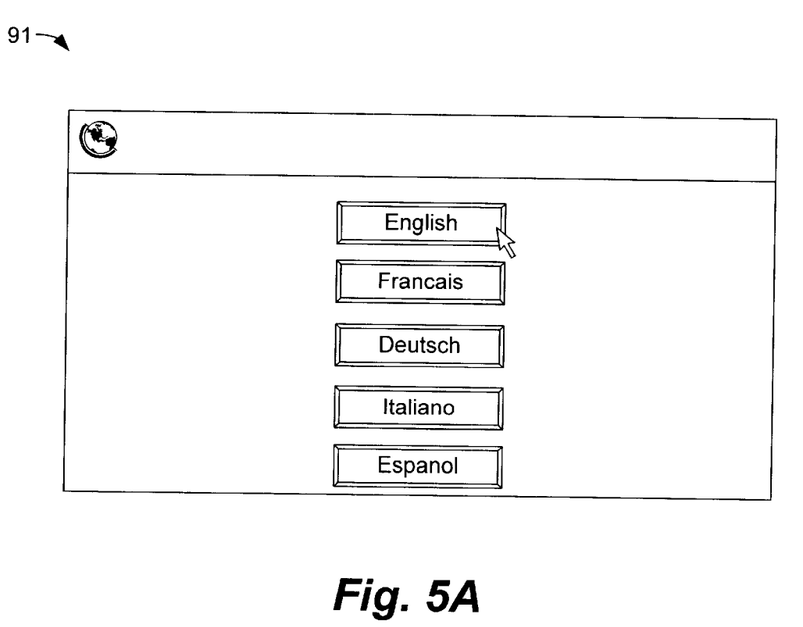
FIGS. 5A through 5C collectively illustrate the geographic localization capability of the ultrasound diagnostic device of FIG. 1.
Figure 5B:
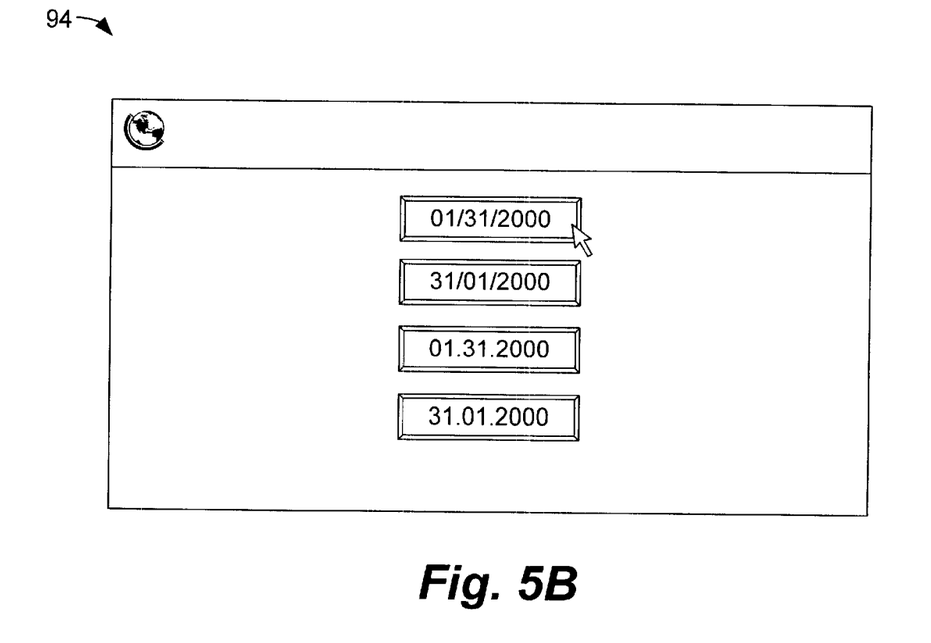
Figure 5C:
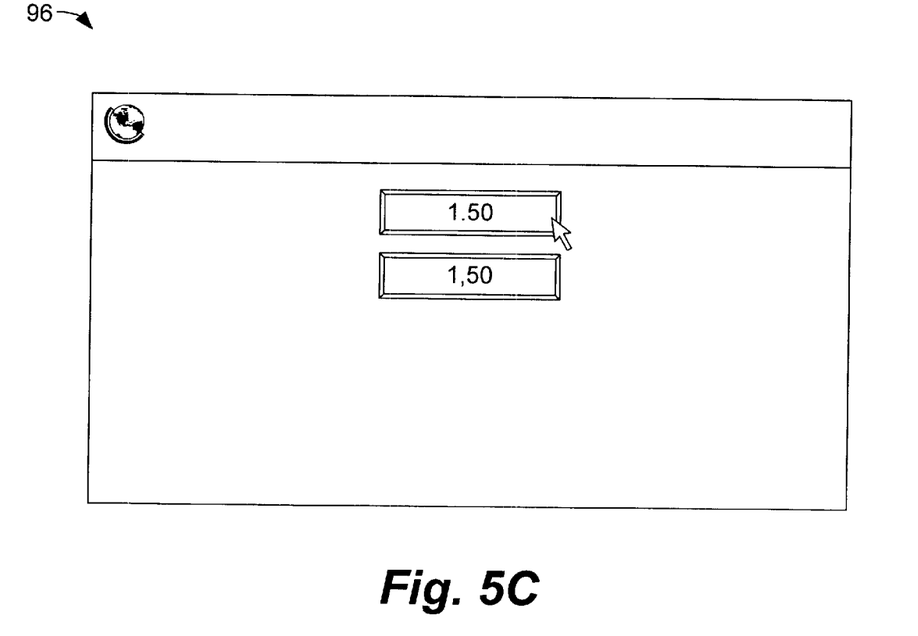

FIGS. 5A through 5C collectively illustrate the geographic localization capability of the ultrasound diagnostic device 10 of FIG. 1. In accordance with this aspect of the invention, the ultrasound diagnostic device 10 can be tailored, or configured, for operation in different languages and locations around the world by the user, thus minimizing translation cost, system verification effort, manufacturing inventory, and selling cost. The control panel 33 and the operating software (not shown) are the same for all languages. Alphanumeric translation requirements are minimized, as only the alphanumeric characters necessary to enter patient identification information are language specific. Screen or control panel text need not be translated.

Localization is streamlined because the operating software is easily expanded and the hardware need not change.

In accordance with this aspect of the invention, the ultrasound diagnostic device 10 provides software configurable choices for several localization items. Specifically, it is possible for the user of the ultrasound diagnostic device 10 to configure local language, the date format and the decimal point character, While these three configurable items are discussed in detail, it is to be understood that additional configurable items may be included within the scope of the invention. The software module that enables the localization for these items is referred to as the localization utility. The localization utility includes three screens that are used by the user to configure the ultrasound diagnostic device 10. The localization utility is invoked by actuating the depth down-arrow button 44 (FIG. 4) and the near field gain down-arrow button 47 (FIG. 4) simultaneously. When the localization utility is invoked, the only active controls are the select button 74, the power on/off button 36 and the touch-pad 66 (FIG. 4). The touch-pad 66 is used to highlight the active value within each screen. The select button 74 allows the user to select the active value and to bring up the next screen in the utility.

The localization utility includes three configurable screens: the language screen (FIG. 5A), the date format screen (FIG. 5B), and the decimal point character screen (FIG. 5C). When the localization utility is invoked as described above, the language screen 91 (FIG. 5A) will be displayed on the display screen 31. The user manipulates the touch-pad 66 and the select button 74 to choose one of the available languages. After selecting one of the languages from the language screen 91, the date format screen 94 (FIG. 5B) will be displayed. The user manipulates the touch-pad 66 and the select button 74 to choose one of the available date formats. Although the date formats shown in FIG. 5B include 01/31/2000; 31/01/2000; 01.31.2000; and 31.01.2000, other date formats are foreseeable. After selecting the date format, the decimal point character screen 96 (FIG. 5C) will be displayed. The user manipulates the touch-pad 66 and the select button 74 to choose either the "." or the "," character to be used as the decimal point character when measurement values are displayed on the display screen 31.

The localization utility can be exited in either of the following two ways. The user actuates the select button 74 and scrolls through the three input screens. Each time the select button 74 is actuated, the setting for that screen is saved to a non-volatile random access memory element (to be described below). Actuating the select button 74 at the third screen (the decimal point character screen 96 (FIG. 5C)), automatically exits the-localization utility and returns the ultrasound diagnostic device 10 to its previous imaging state. The other way in which a user may exit the localization utility is to actuate the power on/off button 36. This exits the localization utility without saving changes to the active screen and powers off the ultrasound diagnostic device 10. Previously saved values in the screens will be retained.

Figure 6:
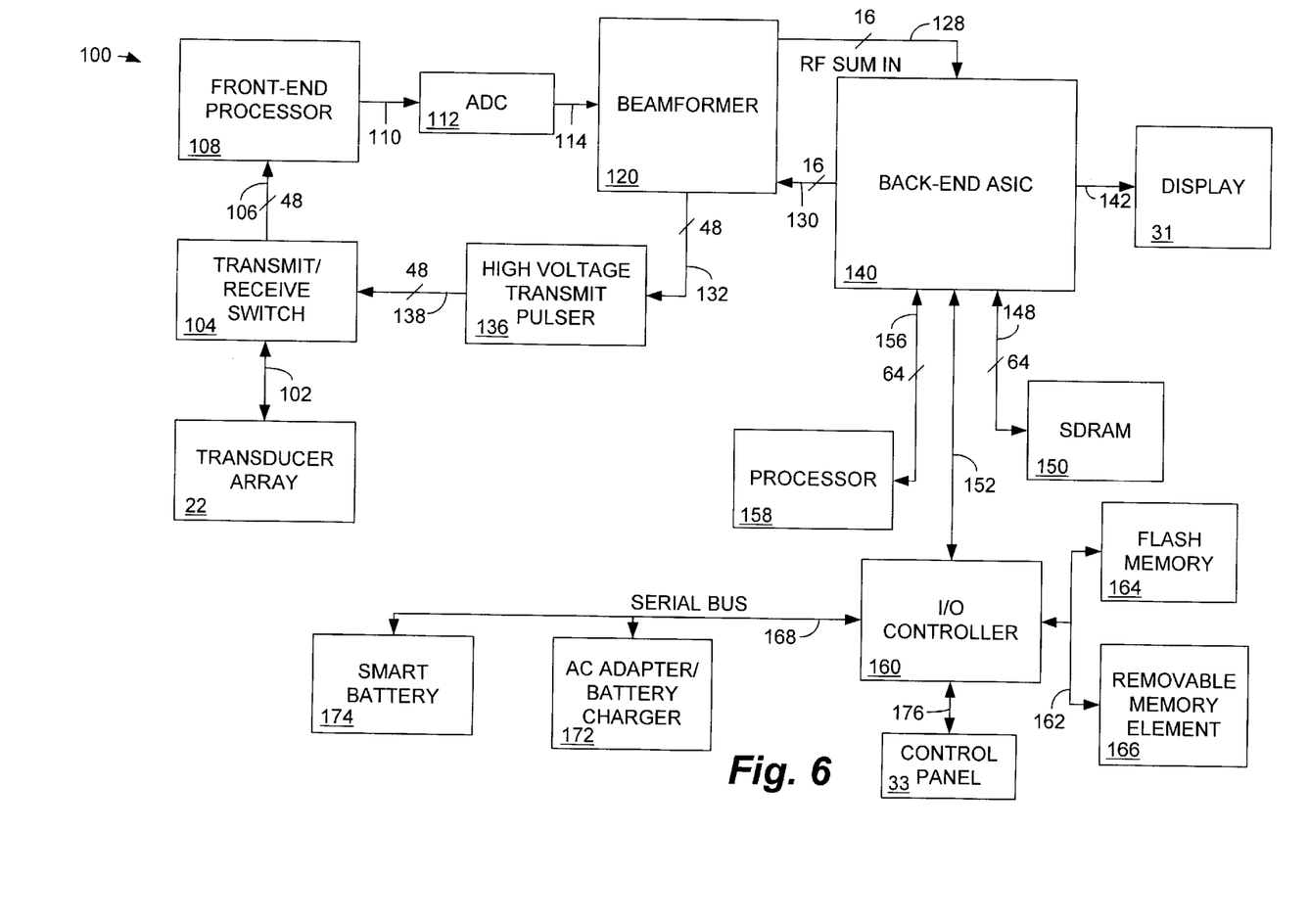
FIG. 6 is a block diagram illustrating the ultrasound diagnostic device of FIG. 1.

FIG. 6 is a block diagram illustrating the ultrasound diagnostic device 10 of FIG. 1. The ultrasound diagnostic device 10 includes transducer array 22, which communicates with transmit receive (T/R) switch 104 via connection 102. In one embodiment, the transducer array 22 can be a sector phased array and is located in transducer handle 19 (FIG. 1) and the connection 102 of FIG. 6 is contained within interface cable 18 of FIG. 1. T/R switch 104 isolates the transmit pulses from the received ultrasound energy and delivers the received signals (one for each transducer element) via connection 106 to processor 108. Processor 108 is typically referred to as a "front-end" processor.

For discussion purposes, transducer array 22 includes 48 transducer elements, resulting in 48 signal channels. However, the transducer array 22 may include more or fewer transducer elements. Furthermore, while illustrated using a single block in FIG. 6, the front-end processor 108 may be implemented as one or more ASICs. The T/R switch 104 also functions as an isolation circuit, thus preventing transmit energy supplied by high voltage transmit pulser 136 via connection 138 (to be described below) from migrating via connection 106 to the sensitive front-end processor 108.

The front-end processor 108 includes a receive processor, which receives each of the received ultrasonic energy signals from each transducer element within transducer array 22 and performs amplification and filtering of the received signals.

The output of front-end processor 108 is supplied via connection 110 to analog-to-digital converter (ADC) 112. ADC 112 digitizes the samples for each channel on connection 110 and supplies an 8-bit digital bit stream for each channel via connection 114 to beamformer 120. The beamformer 120 may contain circuitry, typically in the form of one or more ASICS, configured to perform receive beamforming on the received ultrasonic signals and, configured to provide the low voltage transmit signal timing via connection 132 to drive the high voltage transmit pulser 136 in accordance with that known to those skilled in the art.

Although illustrated using a single block, there is one high voltage transmit pulser 136 used to drive each transducer element within transducer array 22. Furthermore, the low voltage transmit pulser signal function and/or the high voltage transmit pulser may be incorporated into one or more ASICs. Further still, the T/R switch 104, front-end processor 108 and the high voltage transmit pulser 136 may also be incorporated, in any combination, into one or more ASICs.

The combined output of the beamformer 120 is taken from an ASIC located within the beamformer 120 via connection 128 and supplied as a 16-bit beamformed signal to the processor 140 as the signal "RF SUM IN." The processor 140 is typically referred to as a "back-end" processor and is typically implemented in one or more ASICs and is therefore typically referred to as a back-end ASIC. Back-end ASIC 140 performs many processing functions and will be described in greater detail with respect to FIG. 7. Back-end ASIC 140 also provides, via connection 130, to beamformer 120 the coefficient data that allows each of the ASICs within beamformer 120 to perform the beamforming function and to perform the transmit timing necessary to generate the low voltage transmit signal timing pulses on connection 132.

The high voltage transmit pulser 136 can be implemented using discrete components or in an ASIC. In either arrangement, the low voltage transmit timing signals are taken from beamformer 120 via connection 132 and supplied to high voltage transmit pulser 136. Transmit pulser 136 then supplies the 48 transmit pulses via connection 138 to T/R switch 104. T/R switch 104 routes these transmit pulses via connection 102 to each corresponding transducer element within transducer array 22. For parallel receive beamformers, the transmit beam would be broadened by appropriate low voltage transmit timing signals allowing parallel adjacent receive beams to be formed.

Back-end ASIC 140 processes the RF SUM IN signal supplied via connection 128 and provides the ultrasonic image via connection 142 where it is displayed on display screen 31. Display screen 31 can be an LCD or any other display capable of displaying the ultrasonic image data. Back-end ASIC 140 also communicates via connection 148 with memory element 150. Memory element 150 is a static/dynamic random access memory element, preferably 32-megabytes or greater in size, and is preferably implemented as a unified memory as described in commonly assigned U.S. Pat. No. 6,106,468 issued on Aug. 22, 2000 to Dowdell, the text of which is incorporated into this document by reference. The memory element 150 is used for intermediate data storage, storing processing code, tables, and all other executable software used by back-end ASIC 140.

Back-end ASIC 140 also communicates via connection 156 with processor 158. Processor 158 is preferably a 7xx series processor sold under the trademark POWERPC, which is a registered trademark of Motorola Corporation. However, any other processor suitable for processing the received ultrasonic signals can be used. The memory element 150 and the processor 158 can be external to the ASICs and modularly implemented, whereby they are scaleable, upgradeable and interchangeable without significant system impact. For example, the memory element 150 can be upgraded without impacting any other element within the ultrasound diagnostic device 10. Similarly, the processor 158 can be upgraded without impacting any other element within the ultrasound diagnostic device 10. As used herein, the term modular indicates that neither the processor 158 nor the memory element 150 is embedded in an ASIC device.

The back-end ASIC 140 also communicates via connection 152 with input/output (I/O) controller 160. I/O controller 160 interfaces to the control panel 33 via connection 176 and controls the input and output tasks of the ultrasound diagnostic device 10. I/O controller 160 also includes serial and parallel ports for the connection of peripheral devices (not shown). I/O controller 160 also communicates via connection 162 with flash memory element 164 and removable memory element 166. Flash memory element 164 is a non-volatile memory that is used to store the current executable software files (sometimes referred to as the "run-time code") that enable the ultrasound diagnostic device 10 to function and also stores the localization configuration information as described above. Removable memory element 166 is a removable storage media and is used to conveniently update the operating system executed by the ultrasound diagnostic device 10. In this manner, software upgrades can be supplied to the ultrasound diagnostic device 10 and stored in flash memory element 164 by using simple, transportable removable memory element 166.

I/O controller 160 also communicates via serial bus 168 with smart battery 174 and alternating current (AC) adapter/battery charger 172. AC adapter/battery charger 172 provides power to the ultrasound diagnostic device 10 in the absence of a battery, and, if present, charges the smart battery 174. In addition, the ultrasound diagnostic device 10 includes a separate standalone battery charger (not shown) for charging the smart battery when the battery is not installed in the system. The serial bus 168 also allows the connection of test and diagnostics equipment through the I/O controller 160.

Figure 7:
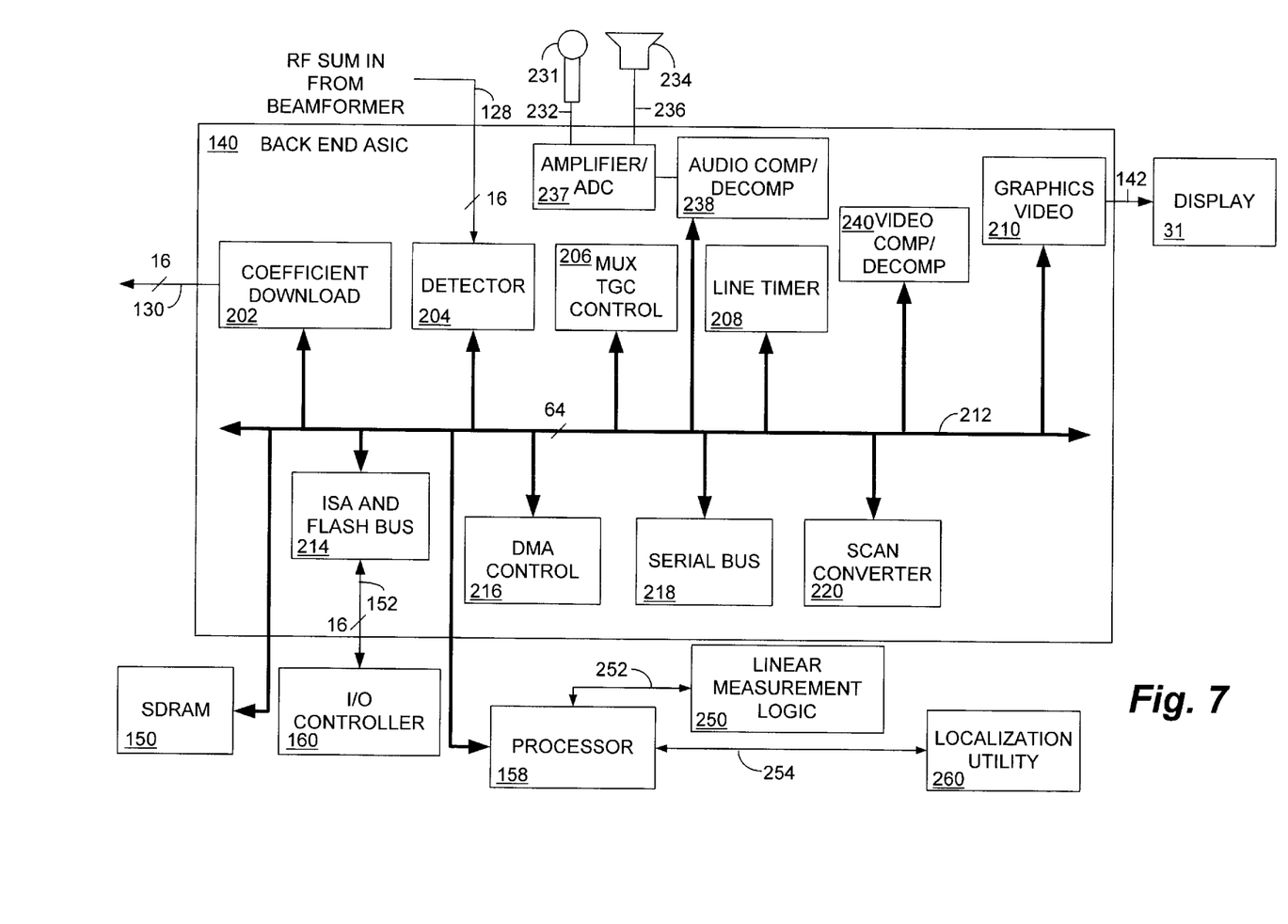
FIG. 7 is a block diagram illustrating the back-end ASIC of FIG. 6.

FIG. 7 is a block diagram illustrating the back-end ASIC 140 of FIG. 6. Back-end ASIC 140 includes coefficient download element 202, which supplies the coefficient data used to load the beamformer 120 (FIG. 6). This data allows the beamformer 120 to perform the beamforming function on the received signal, and to provide the low voltage transmit signal timing information as described above.

The beamformed digital signal labeled RF SUM IN is supplied to the detector 204 via connection 128. The detector 204 receives the digital signal via connection 128 and provides, among other functions, time gain compensation (TGC). TGC is used when receiving ultrasound signals from multiple depths within the target. In such an instance, in order to compensate for the increasing time of flight with respect to depth of the ultrasonic energy, gain is typically increased correspondingly. Detector 204 also provides filtering and performs a detection function in which the input RF signal is converted to a baseband signal, while preserving the phase and amplitude information contained in the signal. Detection includes converting the RF data stream produced on connection 128 into log magnitude data sampled for two dimensional anatomical imaging as well as baseband quadrature data for use in two dimensional color flow imaging. For parallel beam formation, the detector would be replicated to process the two receive beams.

After detection, the data is in the form of log detected amplitude data for anatomic imaging and quadrature detected components (in-phase and quadrature) of the RF signal received from beamformer 120 via connection 128. This data is stored in memory element 150. The information is transferred from the detector 204 to the memory element 150 via bus 212. Bus 212 is, in this embodiment, 64 bits wide.

For each sector scan line transmitted by the transducer array 22 (FIG. 6), a line of RF data is stored in memory element 150 as described above. This process continues with each sector scan line advanced by an amount consistent with the desired lateral resolution and spatial coverage. For example, each line transmitted by the transducer array 22 is at an angle different from the previously transmitted line. For each sector scan line the detector detects the RF energy and stores the values in memory element 150 until a complete frame of data is stored within memory element 150. This data frame is referred to as an acoustic frame of data. When a complete acoustic frame is captured in memory 150, the processor 158 sets up a pointer in memory element 150 indicating the location in memory element 150 where the next acoustic frame will be written. The previous location in memory 150 (also tagged by a memory pointer) containing the latest acoustic data frame will be left intact.

After the latest acquired acoustic frame is stored in memory element 150, the scan converter 220 receives, from the processor 158, the pointer that indicates the location in memory 150 where the latest acoustic frame is stored. The scan converter 220 uses consecutive acoustic scan lines within that stored acoustic data to create a scan converted sector slice for transfer via bus 212 to another location in memory 150. A sector slice is defined as the image area between two adjacent acoustic scan lines. The scan converter 220 continues processing additional slices until all the acoustic data for the current acoustic frame has been scan converted. When the scan converter 220 completes the acoustic frame, an interrupt is sent to the processor 158 indicating that the scan converter 220 has completed the current acoustic frame. When the interrupt is received by the processor 158, the image frame data is read out of memory 150 in raster fashion via bus 212 under control of the graphics video element 210 for output via connection 312 to display screen 31. The graphics video element 210 combines all graphics overlays such as text and cursors with the acoustic frame concurrent with raster readout to the display via connection 142 for viewing on display screen 31.

The back-end ASIC 140 also includes an amplifier/analog-to-digital (ADC) element 237 adapted to receive audio input from an audio input device, such as microphone 231 via connection 232 and adapted to provide an audio signal output via connection 236 to speaker 234.

In accordance with another aspect of the invention, the ultrasound diagnostic device 10 allows the user to generate audio files, which are appended to the ultrasound images to which they correspond. To accomplish this goal, the control panel 33 of the ultrasound diagnostic device 10 has an audio input port (not shown) adapted to allow an audio input device, such as a microphone 231, to be coupled to the back-end ASIC 140. The amplifier/ADC element 237 receives analog signals from the audio input device 231 and performs amplification and analog-to-digital conversion to obtain a digital audio image. The processor 158 may then cause the digital audio image information to be compressed by audio compressor/decompressor element 238 and to be stored in memory element 150. When so instructed by the user via control panel 33, the audio data is stored in or retrieved from memory element 150.

The processor 158 also determines which audio information corresponds to the associated image information stored in the memory element 150. The processor 158 can perform this function in a plurality of ways, as will be understood by those skilled in the art. For example, the processor 158 can be programmed to tag the audio files with tags, which associate the audio files with their respective image files. When the audio files and the image files are stored in the memory element 158, the tags which associate the audio files with the image files are also stored in the memory element 158. The audio files can be associated with the image files by using other techniques, such as, for example, storing audio files and image files in such a manner and in accordance with a predetermined ordering convention that the processor 158 can easily determine which files are audio files, which files are image files, and which image files are associated with which audio files. Those skilled in the art will understand the manner in which this can be accomplished.

Under control of the processor 158, audio files may be read out of the memory element 150, decompressed, if necessary, by the audio compressor/decompressor element 238, and played back over audio output device 234. The image files may be read out of memory element 150 decompressed, if necessary, in video compressor/decompressor element 240, and displayed on the display screen 31. Also, the audio files and the image files may be transferred to the removable memory element 166 (FIG. 6), removed from the ultrasound diagnostic device 10 and placed in an external read/write device (not shown) to allow the image information and the audio information to be downloaded from the memory element 150 to an external computer or memory device. As will be understood by those skilled in the art, the external computer will be programmed to allow the image files and audio files to be read off of the removable memory element 166, decompressed, if necessary, and presented to the user via appropriate output devices.

It should be noted that the audio compressor/decompressor element 238 and the video compressor/decompressor element 240 may be implemented in hardware, software, or in a combination of hardware and software, and need not be implemented within back-end ASIC 140, as will be understood by those skilled in the art. Several audio and video compressors and decompressors are available in the market that are implemented entirely in hardware or entirely in software, or in a combination of hardware and software. The video compression and decompression can be performed in accordance with several well known standards, such as the well known JPEG standard, which is a standard algorithm for compressing and decompressing still images. A wavelet compression algorithm is another example of a compression algorithm that may also be used for this purpose. JPEG compression and decompression algorithms can be performed in hardware using a particular integrated circuit or in software being executed on a microprocessor. Wavelet compression algorithms can also be performed in hardware and/or software.

A suitable video integrated circuit chip for performing video compression and decompression is produced by Zoray Corporation and is marketed as model number ZR36050. This particular video integrated circuit chip utilizes the JPEG compression standard. With respect to audio compression and decompression, several standard compression/decompression algorithms are available on the market. For example, a computer program including an ADPCM Codec, which is commonly supplied with Windows 95 or 98 by Microsoft Corporation of Redmond, Washington, is suitable for performing audio compression/decompression. An audio compression/decompression integrated circuit chip which is suitable for performing audio compression and decompression is manufactured by Cirrus Logic and is sold as model number CS4215.

The direct memory access (DMA) controller 216 acts as a gating function for all data travelling on bus 212. For example, the DMA controller 216 determines whether the scan converter 220 or the detector 204 can access the memory element 150. The DMA controller 216 operates as known to those having ordinary skill in the art.

The international standards architecture (ISA) and flash bus element 214 communicates via connection 152 with I/O controller 160 in order to communicate with the flash memory element 164 and the removable memory element 166 of FIG. 6. The flash memory element 164 provides non-volatile memory storage and includes the run-time software and the localization settings. The removable memory element 166 is used to change and upgrade the operating software when revisions or updates become available. Furthermore, images can be read from the back-end ASIc 140 and written to the removable memory element 166 for transport to other systems.

The line timer 208 represents a series of timers that are used by the processor 158 to provide timing and control functionality. Because all the functionality described with respect to FIG. 7 is timed, the line timer 208 provides this auxiliary timing function, thus off-loading that timing responsibility from the processor 158.

The multiplexer (MUX) TGC control element 206 is employed if a linear or a curved linear array transducer is used. In such a case, the multiplexer function of the MUX TGC control element 206 multiplexes each element of the linear or curved linear array. When a linear or curved linear array is used, a reduced number of elements are processed at any given time and a smaller than the whole number of elements is operational at any given time. Thus, reordering of the elements with respect to the processing channels is required, as those skilled in the art will recognize. The TGC portion of the MUX TGC control element 206 provides both front-end and back-end time gain compensation as described above. The back-end RGC is performed in the detector 204 in FIG. 7 and front-end TGC is performed in the front-end processor 108 of FIG. 6.

The processor 158 also communicates with linear measurement logic 250 and the localization utility 260 via connections 252 and 254, respectively. The linear measurement logic 250 allows a user of the ultrasound diagnostic device 10 to perform the linear depth and distance measurements described above with respect to FIG. 4. The localization utility 260 includes the program code, which is stored in the memory 150 and executed by the processor 158, that allows the ultrasound diagnostic device 10 to be localized as described above with respect to FIGS. 5A through 5C. The linear measurement logic and localization utility are software programs residing in the SDRAM memory 150 and executed by the processor 158 based on the control key selected and are illustrated as separate elements for clarity. There is no other hardware associated with this functionality.

It will be apparent to those skilled in the art that many modifications and variations may be made to the preferred embodiments of the present invention, as set forth above, without departing substantially from the principles of the present invention. For example, through integration and the judicious selection of components, the size and weight of the ultrasound diagnostic device may be further reduced. All such modifications and variations are intended to be included herein within the scope of the present invention, as defined in the claims that follow.

What is claimed is:

1. A portable ultrasound diagnostic device, comprising:
   a control panel having at least one input device, the at least one input device capable of being actuated by a user to enable the user to input commands on the control panel;
   control circuitry electrically coupled to the at least one input device, the control circuitry comprising a processor, which detects when the at least one input device has been actuated and which performs a predetermined imaging or information function in response to a determination that the at least one input device has been actuated; each function being associated with one input device; and
   a display electrically coupled to the control circuitry, the display configured to display information to the user, wherein the control panel and the display comprise a user interface of the ultrasound diagnostic device.

2. The ultrasound diagnostic device of claim 1, wherein the control panel further comprises:
   a plurality of input devices, at least one of the input devices being a touch-sensitive digitizer, and wherein a plurality of the input devices are buttons having icons on them, each button corresponding to a predetermined function to be performed by the control circuitry, wherein the icons on the buttons indicate the functions that are associated with the buttons.

3. The ultrasound diagnostic device of claim 2, wherein the icons are repeated on the display and the icons are associated with the current value of the associated button.

4. The ultrasound diagnostic device of claim 1, further comprising linear measurement logic configured to allow the user to perform a linear measurement of a feature on the display.

5. The ultrasound diagnostic device of claim 4, wherein the linear measurement logic is responsive to one of the input devices and the touch-sensitive digitizer.

6. The ultrasound diagnostic device of claim 4, further comprising:
   a transducer coupled to the control circuitry, the transducer having a transducer face; and
   wherein the linear measurement logic measures a distance between the transducer face and an object being imaged by the ultrasound diagnostic device.

7. The ultrasound diagnostic device of claim 1, further comprising localization logic configured to allow the ultrasound imaging device to be configured in a plurality of configurations by the user.

8. The ultrasound diagnostic device of claim 7, wherein the localization logic allows the ultrasound diagnostic device to be configured for a plurality of different languages.

9. The ultrasound diagnostic device of claim 7, wherein the localization logic allows the ultrasound diagnostic device to be configured for a plurality of different date code styles.

10. The ultrasound diagnostic device of claim 7, wherein the localization logic allows the ultrasound diagnostic device to be configured for a plurality of different decimal point styles.

11. The ultrasound diagnostic device of claim 1, further comprising a transducer coupling port adapted to couple one of a plurality of different transducers to the control circuitry.

12. The ultrasound diagnostic device of claim 11, wherein the control panel, the control circuitry, the display, and a transducer weigh less than fifteen (15) pounds.

13. The ultrasound diagnostic device of claim 11, wherein the control panel, the control circuitry, the display, and a transducer weigh less than six (6) pounds.

14. A portable ultrasound diagnostic device, comprising:
   a control panel having at least one input device, the at least one input device capable of being actuated by a user to enable the user to input commands on the control panel;
   control circuitry electrically coupled to the at least one input device, the control circuitry comprising a host processor, which detects when the at least one input device has been actuated and which performs a predetermined function in response to a determination that the at least one input device has been actuated;
   a display electrically coupled to the control circuitry, the display configured to display information to the user, wherein the control panel and the display comprise a user interface of the ultrasound diagnostic device; and
   localization logic contained in the control circuitry, the localization logic configured to allow the ultrasound diagnostic device to be configured by a user in a plurality of configurations.

15. The ultrasound diagnostic device of claim 14, wherein the localization logic allows the ultrasound diagnostic device to be configured for a plurality of different languages.

16. The ultrasound diagnostic device of claim 14, wherein the localization logic allows the ultrasound diagnostic device to be configured for a plurality of different date code styles.

17. The ultrasound diagnostic device of claim 14, wherein the localization logic allows the ultrasound diagnostic device to be configured for a plurality of different decimal point styles.

18. An ultrasound diagnostic device for obtaining ultrasound diagnostic measurements, the device comprising:
   a control panel having at least one input device disposed thereon, said at least one input device capable of being actuated by a user to enable the user to input commands on the control panel;
   control circuitry electrically coupled to said at least one input device, the control circuitry comprising a host processor which detects when said at least one input device has been actuated and which performs a predetermined function in response to a determination that said at least one input device has been actuated;

a display electrically coupled to the control circuitry, the display configured to display information to the user; and an audio input device connection adapted to enable an audio input device to be electrically coupled to the control circuitry to thereby allow the user to input audio information into the ultrasound diagnostic device for subsequent output, wherein the control panel, the display and the audio input device connection comprise a user interface of the ultrasound diagnostic device.

19. The ultrasound diagnostic device of claim 18, wherein the host processor is configured to associate audio files with image files, the audio files corresponding to audio input information received by the control circuitry from an audio input device connected to the audio input device connection, the image files corresponding to image information received by the control circuitry from a transducer electrically coupled to the ultrasound diagnostic device, the host processor associating one or more audio files with one or more image files by determining which audio files were generated during a period of time in which images associated with said one or more image files were being displayed on the display monitor.

20. A portable ultrasound diagnostic device, comprising:

a control panel having a plurality of input devices, each input device corresponding to one of a plurality of predetermined imaging or information functions, the plurality of input devices and predetermined imaging or information functions being a subset of a larger set of imaging or information functions, at least one input device capable of being actuated by a user to enable the user to input commands on the control panel; each function being associated with one input device;

control circuitry electrically coupled to the at least one input device, the control circuitry comprising a processor, which detects when the at least one input device has been actuated and which performs the predetermined imaging or information function in response to a determination that the at least one input device has been actuated; and a display electrically coupled to the control circuitry, the display configured to display information to the user, wherein the control panel and the display comprise a user interface of the ultrasound diagnostic device.

21. The ultrasound diagnostic device of claim 20, wherein the control panel has less than 30 input devices.

22. The ultrasound diagnostic device of claim 20, wherein the control panel has less than 20 imaging input devices.

* * * * *